United States Patent
Ochs

(10) Patent No.: US 7,325,554 B2
(45) Date of Patent: Feb. 5, 2008

(54) DENTAL DEVICE WITH IMPROVED RETENTION OF A FLAVOR AND/OR CHEMOTHERAPEUTIC AGENT COMPOSITION

(75) Inventor: Harold D. Ochs, Flemington, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 11/239,515

(22) Filed: Sep. 29, 2005

(65) Prior Publication Data

US 2006/0042650 A1    Mar. 2, 2006

Related U.S. Application Data

(63) Continuation-in-part of application No. 11/065,766, filed on Feb. 25, 2005, now abandoned, which is a continuation of application No. 10/805,737, filed on Mar. 22, 2004.

(51) Int. Cl.
*A61C 15/00* (2006.01)
(52) U.S. Cl. ................................................. 132/323
(58) Field of Classification Search ......... 132/322–329
See application file for complete search history.

(56) References Cited

U.S. PATENT DOCUMENTS

| 1,874,433 | A | * | 8/1932 | Briggs ..................... 132/296 |
| 2,354,454 | A | | 7/1944 | Geffner |
| 2,872,929 | A | * | 2/1959 | Rice .......................... 132/323 |
| 3,631,869 | A | | 1/1972 | Espinosa |
| 4,026,308 | A | | 5/1977 | Krivit |
| 4,192,330 | A | | 3/1980 | Johnson |
| 5,105,840 | A | | 4/1992 | Giacopuzzi |
| 5,165,913 | A | | 11/1992 | Hill |
| 5,388,600 | A | | 2/1995 | Hart |
| 5,483,982 | A | * | 1/1996 | Bennett et al. ............. 132/323 |
| 5,570,709 | A | * | 11/1996 | Haddad et al. ............. 132/322 |
| 5,692,531 | A | | 12/1997 | Chodorow |
| 5,819,769 | A | | 10/1998 | Gutierrez |
| 6,085,760 | A | | 7/2000 | Chodorow |
| D497,222 | S | * | 10/2004 | Ochs et al. .................. D28/68 |
| 7,059,334 | B2 | * | 6/2006 | Dougan et al. ............ 132/323 |
| 2003/0098037 | A1 | | 5/2003 | Dougan et al. |
| 2003/0140936 | A1 | * | 7/2003 | Yuhara ....................... 132/307 |
| 2004/0163666 | A1 | * | 8/2004 | Ochs et al. ................. 132/323 |

(Continued)

FOREIGN PATENT DOCUMENTS

EP        0 610 227 B1    8/1994

(Continued)

OTHER PUBLICATIONS

European search report dated Oct. 27, 2005, for corresponding EP application 05251711.7.

*Primary Examiner*—Todd E. Manahan
*Assistant Examiner*—Rachel A. Running

(57) ABSTRACT

A dental floss holder including: a base portion; a pair of spaced-apart jaws extending from the base portion to accommodate a length of dental floss there-between; the spaced-apart jaws having at least one cavity for loading a composition containing flavor and/or a chemotherapeutic agent; and at least one flange for each cavity is disclosed. The dental floss holder provides an improved means for retaining flavor and or chemotherapeutic compositions within the cavity until the dental floss holder is used.

14 Claims, 5 Drawing Sheets

U.S. PATENT DOCUMENTS

2004/0200497 A1* 10/2004 Thorpe et al. ............... 132/287
2005/0172982 A1* 8/2005 Ochs et al. .................. 132/323

FOREIGN PATENT DOCUMENTS

| | | | |
|---|---|---|---|
| EP | 1 579 822 A | 9/2005 | |
| JP | 8173243 A | 7/1996 | |
| WO | WO 03/043523 A1 | 5/2003 | |

* cited by examiner

FIG. 4
FIG. 5
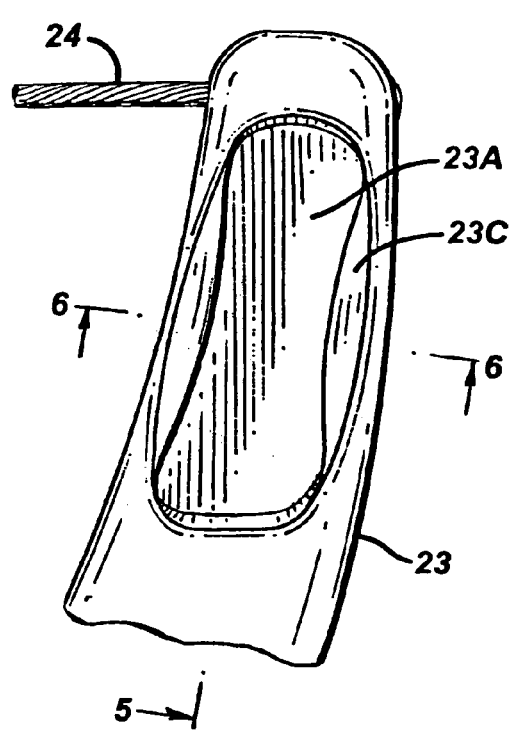
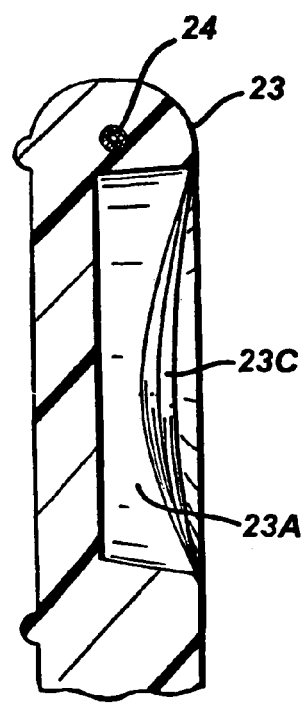
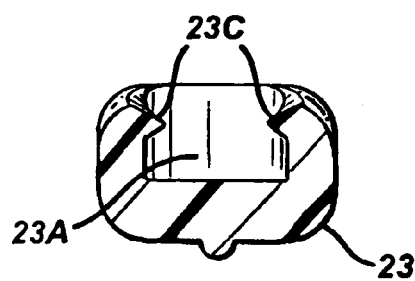
FIG. 6

US 7,325,554 B2

DENTAL DEVICE WITH IMPROVED RETENTION OF A FLAVOR AND/OR CHEMOTHERAPEUTIC AGENT COMPOSITION

This application is a continuation-in-part of application Ser. No. 11/065,766, filed Feb. 25, 2005, now abandoned, which is a continuation of application Ser. No. 10/805,737, filed Mar. 22, 2004.

BACKGROUND OF THE INVENTION

1. Field of the Invention

The present invention relates to a dental device that can deliver flavor and/or chemotherapeutic agents to the mouth. The device contains improved means for retaining the flavor and/or chemotherapeutic agent composition.

2. Description of the Prior Art

The desire for adding flavor to the mouth and teeth while flossing has led to the development of flavored dental floss coatings. Dental flosses having flavoring applied directly to the floss are well known in the art. In use, flavored dental floss is inserted between teeth. The dental floss leaves a light flavoring in the mouth as the floss is passed between teeth.

Flavored dental floss is typically packaged and sold in lots of twenty-four or thirty-six units. The process for making flavored dental floss typically involves placing a traditional flavor system including flavor such as spray dried flavor in a coating such as a microcrystalline wax, then applying the coating to a fiber substrate to generate a dental floss. Dental floss holders have recently become a popular way of flossing between teeth. If these wax-coated dental flosses are used in an injection molding process for making dental floss holders, the coating will eventually clog the injection mold and cause the molding machine to jam. Furthermore, the amount of flavor available is small and thus only a hint of flavor can be provided through this technique.

A Controlled Release Interproximal Delivery System is disclosed in U.S. Pat. No. 5,165,913, wherein the dental floss contains surfactant and silicone preparations with added chemotherapeutic agents.

Unlike the present invention, the '913 patent provides flavor only to the floss, allowing for just a small amount of flavoring to be inserted into a user's mouth.

Co-pending U.S. patent application Ser. No. 10/805,737, filed Mar. 22, 2004, the disclosure of which is hereby incorporated by reference, teaches a dental floss holder having means for retaining flavor and/or active compositions. The means for retaining the compositions include through holes and anchors.

Although the device taught in the co-pending patent application is useful, there is a need for such a device with improved means for retaining the flavor and/or active composition in the device until used.

SUMMARY OF THE INVENTION

In a first embodiment, the present invention provides a dental floss holder including: a base portion; a pair of spaced-apart jaws extending from the base portion to accommodate a length of dental floss there-between; the spaced-apart jaws having at least one cavity for loading a composition containing flavor and/or a chemotherapeutic agent; and at least one flange for each cavity.

The dental floss holder includes a base portion and a pair of spaced-apart arms extending from the base portion. A length of dental floss is secured between the distal ends of the spaced-apart arms. The base portion may have a pair of lateral sides and means for releasable engagement for attachment to a handle. Each lateral side may include at least one protrusion and at least one indentation spaced laterally there-from. When present, the protrusion on the first lateral side is located opposite the indentation on the second lateral side. The indentation on the first lateral side is located opposite the protrusion on the second lateral side.

The spaced-apart arms have at least one cavity that is adapted to be capable of holding a flavoring agent, a chemotherapeutic agent or a combination thereof. Each cavity can be a through hole or a concaved area. A solid or semi-solid composition having flavoring agent and/or a chemotherapeutic agent is loaded therein. Each cavity is provided with a flange that is adapted to retain the composition within the cavity until the floss holder is used. That is, the composition containing flavoring agent and/or a chemotherapeutic agent is mechanically restrained within the cavity by the at least one flange until such time as the floss holder is contacted by a user's saliva. The flange acts to reduce a portion of the open area defined by the cavity and thus restrict the composition from falling out prematurely. Once flossing begins, the composition containing flavoring agent and/or a chemotherapeutic agent disperses throughout the mouth as each cavity filled with flavoring contacts saliva from the user's mouth.

In a second embodiment, the present invention provides a dental floss device having an integrally connected dental floss holder and handle. The dental floss holder comprises a base portion and a pair of spaced-apart arms extending from the base portion to accommodate a length of dental floss there between. Each spaced apart arm has at least one cavity defined therein. Each cavity may be in the form of a through hole or a concavity capable of containing compositions having flavoring agent and/or a chemotherapeutic agent. The composition containing flavoring agent and/or a chemotherapeutic agent is retained in the cavity by at least one flange until the floss holder is used. The base portion comprises a pair of lateral sides. The handle integrally extends from the base portion of the dental floss holder. In use, the floss holder has an integrally attached handle at its base portion. The consumer places the floss holder portion in their mouth to begin flossing. Once the floss from the floss holder is inserted between the user's teeth and saliva contacts the composition having flavoring agent and/or a chemotherapeutic agent stored in each arm's cavity, the flavoring and/or chemotherapeutic agent disperses throughout the user's mouth.

In a third embodiment, the present invention provides a dental floss device including a handle having a head portion and a flavored dental floss holder, which is adapted to be releasably connected to the head portion for subsequent use. The dental floss device further includes releasable engagement means for releasably securing the dental floss holder to the handle during use. The head portion extends transversely of the longitudinal axis of the gripping portion, as a result of which the handle has a generally T-shaped configuration. The head portion includes a generally U-shaped channel for releasably receiving the above-described dental floss holder. The U-shaped channel has a floor and two spaced apart walls. A first of the two walls includes at least one protrusion and at least one indentation spaced laterally therefrom. The second of the two walls defining the U-shaped channel also includes at least one protrusion and at least one indentation spaced laterally therefrom. The protrusion on the first of the two walls is located opposite the indentation on the second of the two walls. The indentation on the first of the two walls is located opposite the indentation on the second of the two walls. The indentation on the first of the two walls is located opposite the protrusion on the second of the two walls. The protrusions and indentations on the two walls defining the U-shaped channel of the head portion are sized and arranged to receive in frictional engagement the indentations and protrusions on the lateral sides of the base portion of the aforementioned dental floss holder. The dental floss holder has a base portion and a pair of spaced-apart arms extending from the base portion to accommodate a length of dental floss there-between. The base portion includes a pair of lateral sides. Each lateral side contains at least one protrusion and at least one indentation spaced laterally there-from. The protrusion on the first lateral side is located opposite the indentation on the second lateral side. The indentation on the first lateral side is located opposite the protrusion on the second lateral side. Preferably, the spaced-apart arms include snap fit projections for engagement with the head portion of the handle. The spaced-apart arms have snap fit projections extending inwardly there-from. Each of the spaced-apart arms has at least one cavity defined therein. Each cavity may be a through hole or a concavity capable of holding a composition containing flavoring agent and/or a chemotherapeutic agent. The composition containing flavoring agent and/or a chemotherapeutic agent is retained in the cavity by at least one flange until the floss holder is used. In use, the floss holder is attached to the handle at its head portion. The consumer then places the floss holder portion in their mouth to begin flossing. Once the floss from the floss holder is inserted between the user's teeth and saliva contacts the flavoring agent and/or chemotherapeutic agent stored in each arm's cavity, the flavoring agent and/or chemotherapeutic agent will disperse throughout the user's mouth.

In a fourth embodiment, the present invention provides a handle having an elongated gripping portion and a head portion. The head portion may be designed for releasably receiving a dental floss holder with a single cavity or multiple cavities in each arm. The head portion may further be releasably engaged to any dental article carrying flavor or chemotherapeutic additives. The dental article may consist of a brush, pad, probe or other device known in the art for delivering flavor or chemotherapeutic additives to the oral cavity. The head portion extends transversely of the longitudinal axis of the gripping portion, as a result of which the handle has a generally T-shaped configuration. The head portion includes a generally U-shaped channel for releasably receiving the above-described dental floss holder. The U-shaped channel comprises a floor and two spaced apart walls. The U-shaped channel may include a cavity on an exterior surface of the two spaced apart walls. Each cavity may have flavoring agent and/or a chemotherapeutic agent loaded therein. The flavoring agent and/or chemotherapeutic agent compositions are retained in the cavity by at least one flange. A first of the two walls includes at least one protrusion and at least one indentation spaced laterally therefrom. The second of the two walls defining the U-shaped channel also includes at least one protrusion and at least one indentation spaced laterally therefrom. The protrusion on the first of the two walls is located opposite the indentation on the second of the two walls. The indentation on the first of the two walls is located opposite the protrusion on the second of the two walls. The protrusions and indentations on the two walls defining the U-shaped channel of the head portion are sized and arranged to receive in frictional engagement the indentations and protrusions on the lateral sides of the base portion of the aforementioned dental floss holder. Alternatively, the head portion may be a conventional toothbrush head or a head portion for housing cavities.

BRIEF DESCRIPTION OF THE DRAWINGS

FIG. 4 is a magnified view of a cavity in the dental floss holder in FIG. 1, in accordance with the present invention;

FIG. 5 is a longitudinal cross-section view taken along line 5-5 of the dental floss holder of FIG. 4;

FIG. 6 is a horizontal cross-section view taken along line 6-6 of the dental floss holder of FIG. 4;

DETAILED DESCRIPTION OF PREFERRED EMBODIMENTS

The present invention is directed to a dental device, such as for example, a dental floss holder that is adapted to be connected to a handle. In the first embodiment of the invention wherein the dental device is a dental floss holder, the dental floss holder includes a base portion and a pair of spaced-apart jaws extending from the base portion to accommodate a length of dental floss there-between. The spaced-apart jaws have at least one cavity for loading a composition containing flavor and/or a chemotherapeutic agent; and at least one flange for each cavity.

Figure 1:
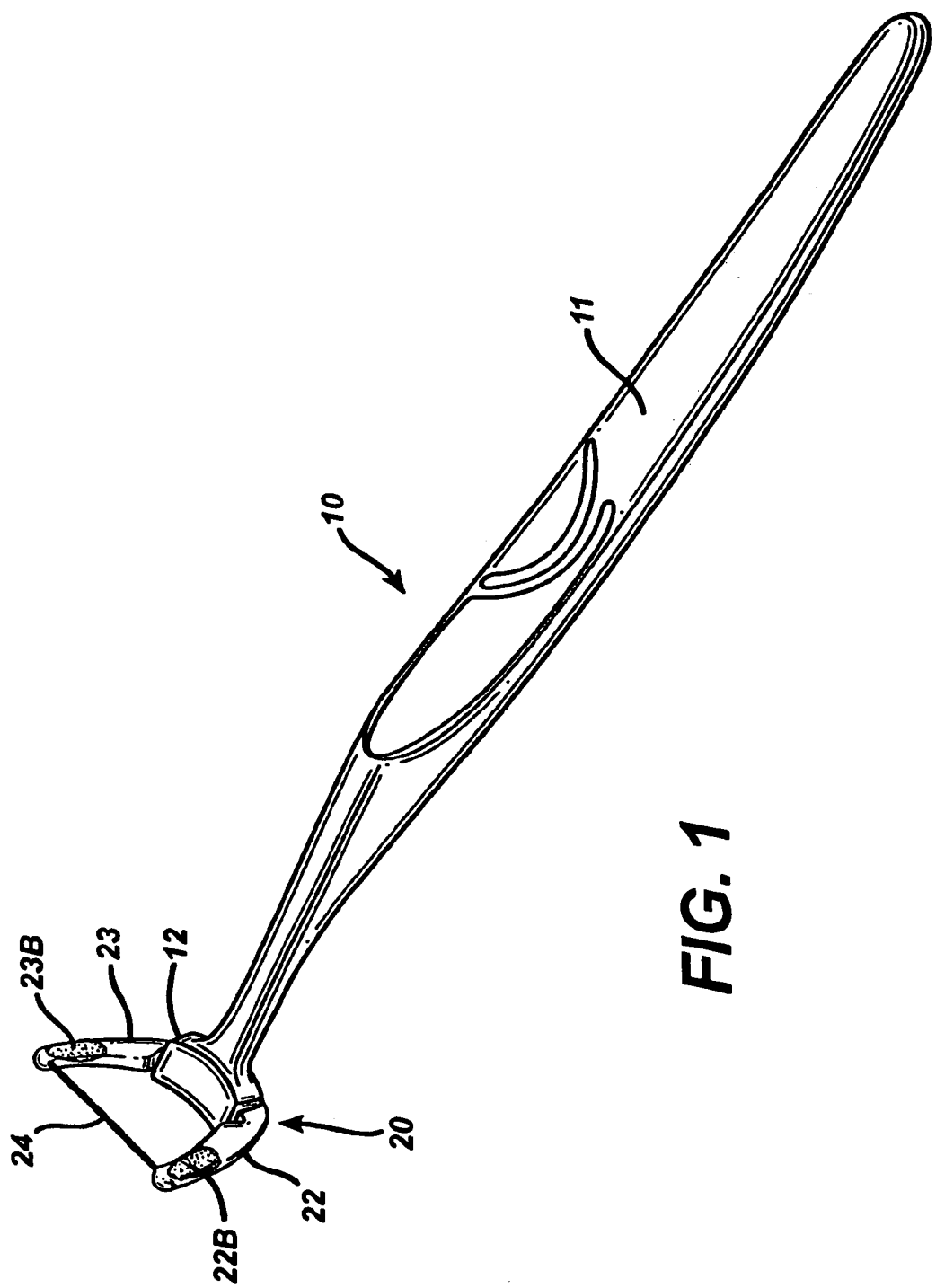
FIG. 1 is a top plan view of one embodiment of a dental floss holder and handle in accordance with the present invention.
Figure 2:
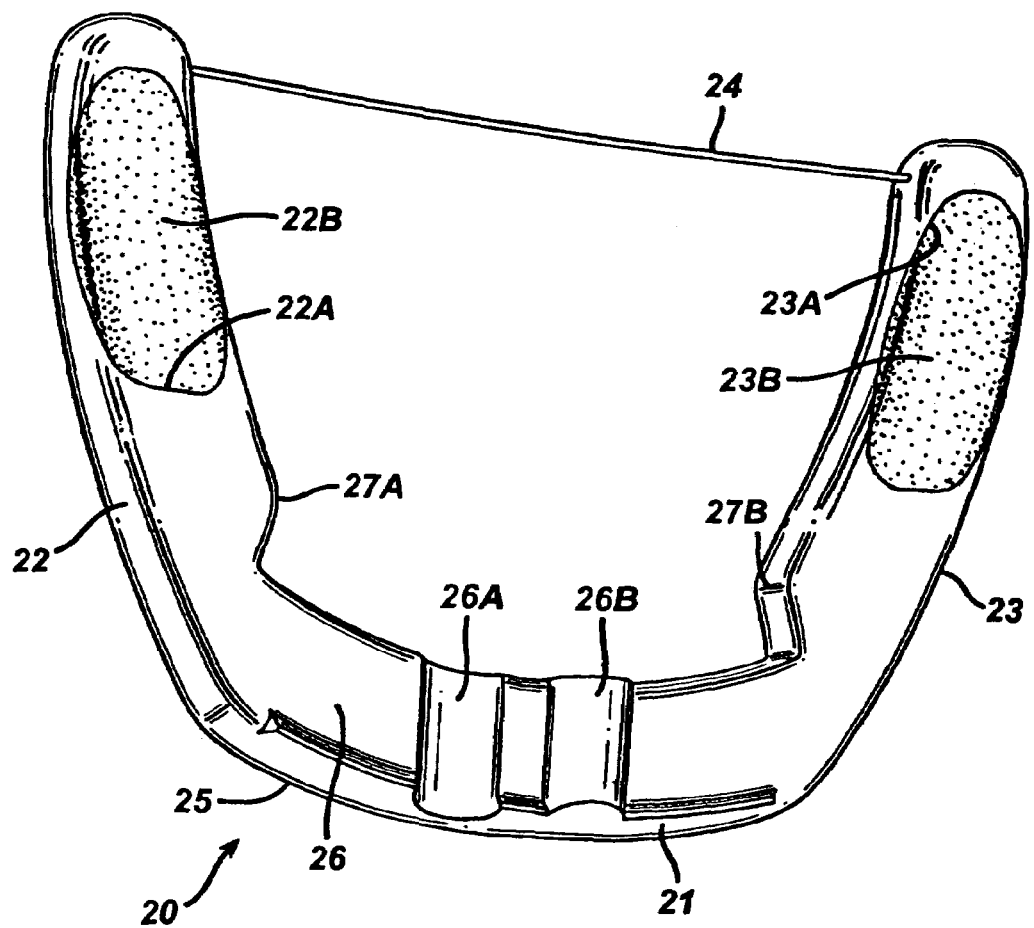
FIG. 2 is a front view of the dental floss holder in FIG. 1, in accordance with the present invention.
Figure 3:
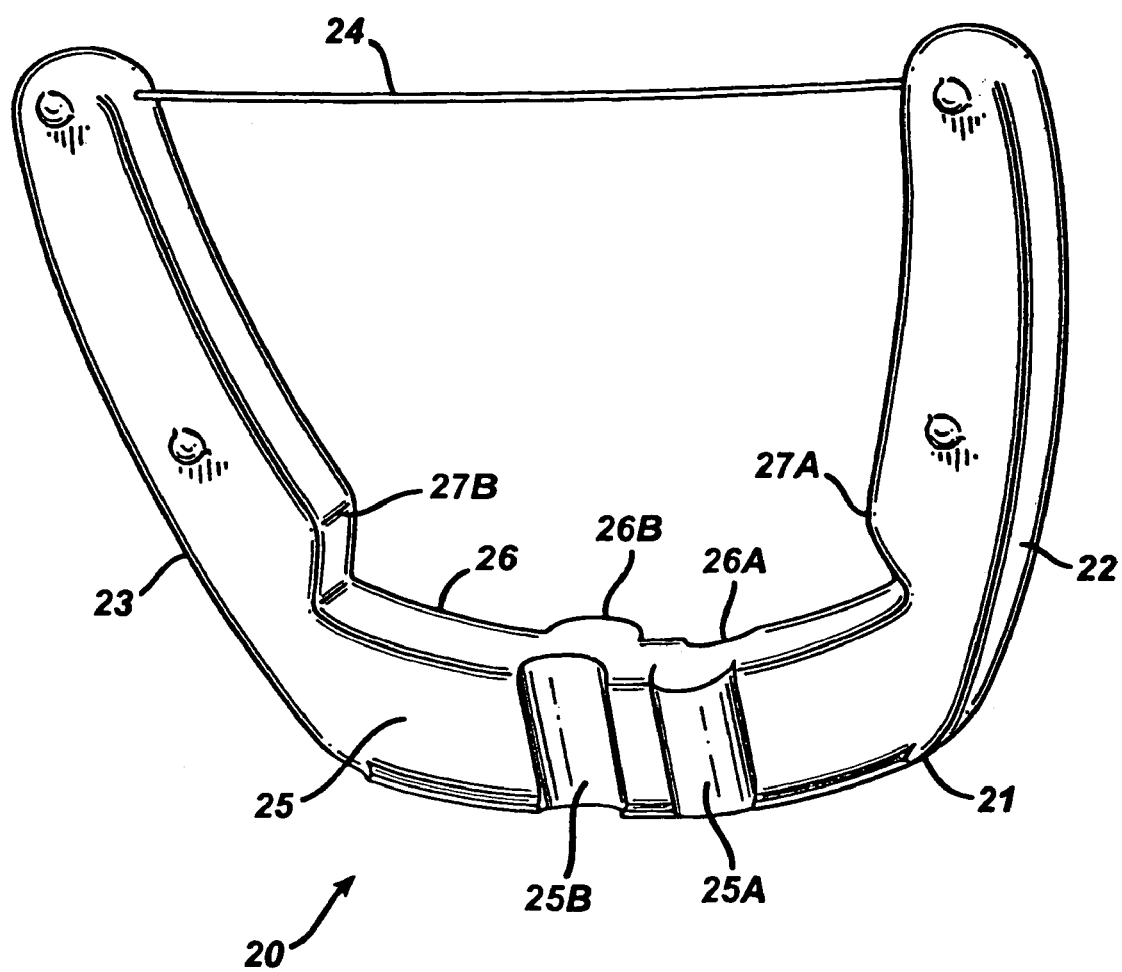
FIG. 3 is a rear view of the dental floss holder in FIG. 1, in accordance with the present invention.
Figure 7:
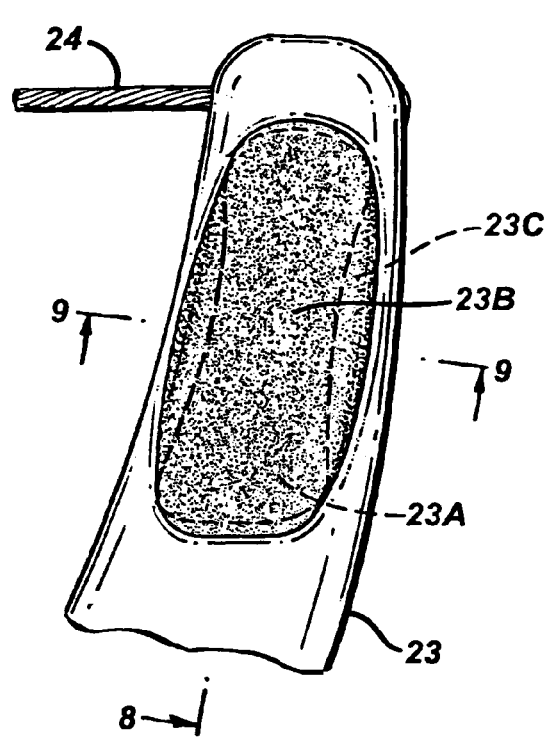
FIG. 7 is a magnified view of a cavity containing a flavor composition in the dental floss holder in FIG. 1, in accordance with the present invention.
Figure 8:
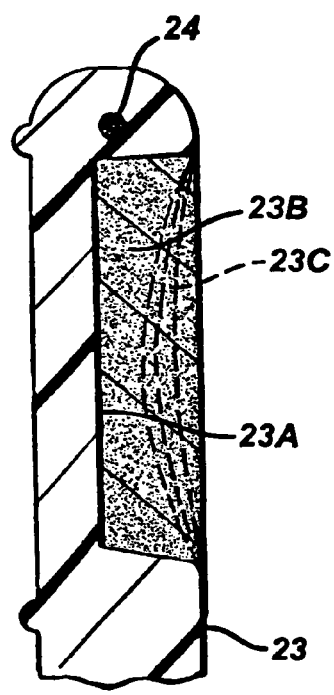
FIG. 8 is a longitudinal cross-section view taken along line 8-8 of the dental floss holder of FIG. 7.
Figure 9:
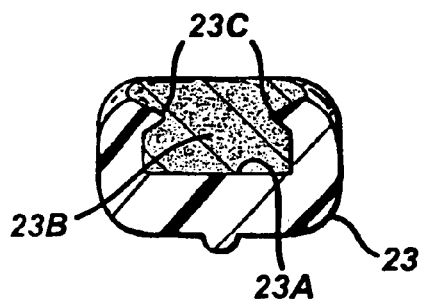
FIG. 9 is a horizontal cross-section view taken along line 9-9 of the dental floss holder of FIG. 7.

Referring to FIGS. 1-3, the dental floss holder 20 includes a base portion and a pair of spaced-apart arms extending from the base portion 21 and a length of dental floss 24 is secured between the distal ends of the spaced-apart arms 22, 23. The dental floss holder 20 retains the length of dental floss 24 for cleaning between teeth. Any dental floss material known in the art may be used in the dental floss holder of the present invention. Examples of suitable dental floss material include, but are not limited to a monofilament fiber or a multi-filament yarn comprising a plurality of such monofilament fibers. The dental floss holder is provided with at least one cavity 22A, 23A, preferably located in at least one of the spaced-apart arms. Each cavity can be a through hole that extends completely through the arm (not shown) or alternatively the cavity may be in the form of a concaved area that extends only partially through the arm. A composition 22B, 23B having flavoring agent and/or a chemotherapeutic agent may be loaded into each cavity 22a, 23a respectively. Referring to FIG. 4-9, the composition containing flavoring agent and/or a chemotherapeutic agent is retained in the cavity by at least one flange 23C until the floss holder is used. Once flossing begins, the composition containing flavoring agent and/or a chemotherapeutic agent disperses throughout the mouth as each cavity filled with flavoring agent contacts saliva from the user's mouth.

The handle and head comprising the dental device of the present invention may be made of any suitable material known in the art. Suitable materials include polymers such as, but not limited to, acrylics, such as poly methyl methacrylate; polyolefins, such as polyethylene and polypropylene; polyesters, such as polycaprolactone; co-polyesters; polycarbonate; and mixtures thereof.

For dental flossing devices, the handle and dental floss holder may be made of the same material or different materials. Preferably, the dental floss holder (exclusive of the dental floss material) is made of a material that is softer than the material from which the handle is made. In a preferred embodiment, the dental floss holder is made from a polypropylene material and the handle is made of co-polyester material.

The devices of the present invention may be made by any suitable process known in the art. Injection molding is preferred. Flanges may be formed by applying sufficient force on the device to deform an upper portion of a surface of the dental floss holder surrounding the cavity. The pressure may be applied by means known in the art, such as the use of a press and the like. A bar or rod may be attached to the press and utilized to minimize the area of contact with the dental floss holder, thereby providing flexibility in the size of the flange(s) by changing the size of the bar or rod.

The dental floss holder includes two spaced-apart arms wherein at least one of the spaced-apart arms has a cavity positioned therein. Each cavity can extend entirely through the arm or the cavity may be in the form of an indentation that is open to only one side of the arm and is thus closed to an opposite side of the arm. In use, each cavity contains a flavoring agent and/or chemotherapeutic agent therein. The shape of the cavity is not, per se, critical to the invention, provided of course that the cavity defines a volume that is sufficient to contain an effective amount of flavoring agent and/or chemotherapeutic agent. In general, the cavity may be in the form of a square, circle, triangle or any shape formed therein. Each cavity is defined by side walls which define a cavity width therebetween.

In accordance with one embodiment of the invention, the cavity may be defined by a pair of opposite side walls wherein one side wall is substantially parallel to an opposite side wall. In a preferred embodiment, at least one side wall is formed at an oblique angle with respect to an outer surface of the arm such that the cavity is wider at the outer surface of the arm and tapers inward as it extends into the thickness of the arm. In a most preferred embodiment, both opposite side walls are formed at an oblique angle with respect to the surface of the arm and thus the side walls of the cavity taper inwards as they extend through the thickness of the arm. In accordance with this embodiment, the cavity has a continuously decreasing width throughout the thickness of the arm.

The cavity is provided with at least one flange that serves as a mechanism to help retain the flavoring agent and/or chemotherapeutic agent within the cavity until such time as the dental device is placed within a user's oral cavity. The flange extends outward from at least a portion of the side wall of the cavity and effectively reduces a portion of the width and/or length of the cavity. Each flange may extend from the side wall of the cavity and be located such that the flange is either located over or into the composition within the cavity. When the flange extends over the composition, it is usually located on or slightly above the surface of the arm. In an alternative embodiment, the flange may be located immediately subjacent to the surface of the arm. In accordance with this embodiment, the flange will extend into the composition since it is located within the cavity in a spaced apart relationship with respect to the surface of the arm. Preferably, each flange may extend from about 0.05 mm to about 1.58 mm from the side wall within the cavity and in use, may extend by the same amount either above or into the composition. In either embodiment, the flange preferably contacts at least a portion of the composition and prevents the composition from being prematurely dislodged from the cavity prior to use. Each flange may be co-extensive in length with the length of the cavity. Typically, the length of each flange may be from about 0.25 mm to about 9.52 mm in length along the top of the cavity. Alternatively, each cavity may contain a plurality of smaller flanges, each flange extending only along a portion of the length of the cavity. For example, the cavity may contain four or more relatively small flanges, for example two flanges on each side of the cavity. In a preferred embodiment, each cavity contains multiple flanges wherein each cavity contains two relatively long flanges, one on each opposite side of the cavity.

It is an important consideration that the composition having flavoring agent and/or a chemotherapeutic agent be in the form of a solid or semi-solid material when at room temperature and that it is capable of being contained within a pre-defined cavity shape. The flavoring agent may be in the form of a water soluble or water insoluble composition that is capable of being filled into the cavity of the dental device. The composition preferably is water soluble and contains flavor droplets, sweeteners and other excipients to form a stable solid or semi-solid composition. The composition may also contain commercially available spray dried flavors. Suitable water soluble compositions may include, but are not limited to, polyethylene glycols ("PEG"), such as PEG 1000 to PEG 5000, ethylene oxide/propylene oxide copolymers, such as those commercially available under the trade name PLURONIC®, and polyvinyl alcohols. These compositions may be heated and stirred and flavor oil may be added to homogenize the flavor system. This homogenization breaks up the flavor into droplets and disperses it into the composition. The composition may be filled into the cavity(s) of the arms where it may cool, solidify and bond. Suitable water insoluble compositions include, but are not limited to, an emulsion of oil and water soluble composition with flavor immersed therein and microcrystalline wax. The water insoluble substance preferably has a low melting point, e.g., below 82 degrees C. and more preferably, e.g., below 60 degrees C. Typically, spray dried flavor is used in conjunction with water insoluble compositions. It should be noted that water insoluble substances yield low flavor delivery when used this way.

The chemotherapeutic agents may also be in the form of a water soluble or water insoluble composition that is capable of being filled into the cavity of the dental device space-apart arms. Chemotherapeutic agents include, but are not limited, antimicrobials such as alkyl trimethyl ammonium bromide, chlorohexidene, sanguinaria, triclosan, zinc sulfate, antibiotics such as tetracycline, antioxidants, desensitizers such as potassium nitrate, remineralizing agents such as compounds of fluoride such as sodium fluoride or stannous fluoride, anti-tartar agents such as tetrasodium pyrophosphate (TSPP), plaque control agents such as cetyl pyridinium chloride, cleaning substances such as surfactants and emulsifiers such as sodium lauryl sulfate, sodium lauryl sacosinate, surfactants such as block co-polymers, coating substances such as silicones, carbowaxes, silicone glycol copolymers and polydimethyl siloxane teeth whitening and bleaching agents such as calcium peroxide, pH buffering agents such as buffered or acidulated phosphofluoride, sodium monofluorophosphate antifungal agents and hemostatic agents such as vitamin K and calcium ions in the form of water-soluble calcium salts.

The composition may also contain moisturizing agents, lubricating agents, effervescent agents, sensory agents, soothing agents, anti-inflammatory agents, and the like and combinations thereof.

The dental floss may be in the form of a multi-filament yarn and may be circular in cross section or flat in cross-section, and typically has a denier ranging from about 200 to about 1400. The denier of the individual filaments forming the yarn typically ranges from about 1 to about 6, although other deniers may be used in some circumstances if desired. The yarn may be twisted or untwisted as well as coated with substances to prevent fraying and provide ease of sliding between teeth.

Psuedo-monofilament yarns may also be used as dental floss material in the present invention. Pseudo-monofilament yarns are made by extruding bi-component fibers comprising a core of one polymer and a sheath of a different polymer, then either partially or totally melting the sheaths of the fibers to bond or fuse the fibers, resulting in a monofilament look and feel. One example of a suitable bicomponent fiber for making pseudo-monofilament yarn is a core of nylon 6 with a sheath of PEBAX® brand polyether/amide copolymer. Other materials besides nylon can be used for the core of the bicomponent fibers and other polymeric materials besides polyether/amide copolymer may be used as the sheath material.

Other dental floss materials which may be used in the present invention include, but are not limited to, nylon 6-6, nylon 6, polypropylene, polyethylene, high molecular weight polyethylene, ultra high molecular weight polyethylene, monofilament polytetrafluoroethylene, and the like materials. Combinations of such materials are also acceptable as long as they provide the floss with strength and resistance to fraying. Ultra high molecular weight polyethylene is a preferred dental floss material.

The individual monofilaments comprising a multifilament dental floss yarn may, if desired, be air entangled. If the yarn is air entangled, the air entanglement nodes may be from about 1.25 cm to about 5.2 cm apart, preferably from 2 cm to 3 cm apart. One type of air entangled yarn is described in U.S. Pat. No. 5,908,039, the disclosure of which is hereby incorporated by reference.

As is known in the art, the dental floss may be twisted. If the dental floss is twisted, it is preferable to have less than 6 turns per 2.54 cm, and more preferably less than 5 turns per 2.54 cm. As is also known in the art, the dental floss may be coated with waxes, flavorants, active ingredients, and the like.

A suitable process of manufacturing dental floss holders includes feeding dental floss through a multi-cavity mold and injecting plastic into the mold to form the holders. This process is discussed more fully in U.S. Pat. No. 5,538,023 to Oczkowski et al., with is incorporated herein by reference in its entirety. After completion of the injection-molding step, the floss may then be cut and tied at the ends. Alternatively, the ends are heated to form spheres and retain the floss material in place. The floss in the dental floss holder typically has some slack. In use, it is preferred that the dental floss be taut.

The relationship between the snap fit projections on the dental floss holder and the terminal snap fit recessions of the head portion may be adapted to make the floss material taut when the dental floss device is assembled for use. The length of the head portion is sized so that when the dental floss holder is secured in the U-shaped channel of the head portion, the distance between the arms of the dental floss holder is increased, thus making the floss material taut. The distance by which the arms of the dental floss holder is increased when the dental floss holder is brought into engagement with the head portion of the handle depends on the amount of slack in the dental floss material when the dental floss holder is out of engagement with the head portion. Typically, this distance ranges from about 0.13 mm to about 1.52 mm, preferably from about 0.25 mm to about 0.51 mm.

Examples are provided below to further illustrate the dental floss devices of the present invention. The invention should not be construed as being limited to the specific details set forth herein.

EXAMPLE 1

Handle

A co-polyester handle according to the present invention was made by injection molding. Referring now to the appended drawings 1-9, handle 10 comprises an elongated gripping portion 11 and a head portion 12 at its distal end. Head portion 12 extends transversely of the longitudinal axis of gripping portion 11, as a result of which handle 10 has a generally T-shaped configuration. Head portion 12 includes a generally U-shaped channel for releasably receiving a dental floss holder of the type mentioned hereinabove and in Example 2. The U-shaped channel comprises a convex floor and two spaced apart walls. The first wall comprises a protrusion and an indentation spaced laterally therefrom. The second wall defining the U-shaped channel comprises a protrusion and an indentation spaced laterally therefrom. The protrusion on the first wall is located opposite the indentation in the second wall. The indentation on the first wall is located opposite the protrusion on the second wall. Referring to FIGS. 1 and 2, the protrusions and indentations on the walls are sized and arranged to receive in frictional engagement mating indentations and protrusions on lateral sides 25, 26 of base portion 21 of the aforementioned dental floss holder 20. See also Example 2 hereinafter. The sides of the head portion 12 engage snap fit projections 27A, 27B of dental floss holder 20 when the floss device is assembled for use.

EXAMPLE 2

Flavored Dental Floss Holder

A polypropylene flavored dental floss holder according to the present invention was made by injection molding with Eastman EASTAR® BR003 co-polyester. As is seen in FIGS. 2 and 3, dental floss holder 20 comprises a base portion 21 and a pair of spaced-apart arms 22 and 23 extending from the base portion to accommodate a length of dental floss 24 therebetween. Base portion 21 is comprised a pair of lateral sides 25, 26. Lateral side 25 comprised a protrusion 25A and an indentation 25B spaced laterally therefrom. Protrusion 25A on first lateral side 25 was located opposite indentation 26A on second lateral side 26. The indentation 25B on first lateral side 25 was located opposite protrusion 26B on second lateral side 26. The spaced-apart arms included snap fit projections 27A, 27B for engagement with the sides of head portion 12 of handle 10. The spaced-apart arms 22 and 23 also had at least one cavity 22A, 23A defined therein for containing composition 22B, 23B that includes a flavoring agent and/or chemotherapeutic agent. As shown in FIGS. 4-9, each cavity 23A contains flanges 23C. The floss holder was machined out to provide each cavity with approximately 0.81 mm wide, by 1.59 mm deep and 9.53 mm long extending proximate the line where the floss passed through the head upward along the centerline of the floss holder. The dental floss 24 was 435 denier SPECTRA® Fiber 1000 ultra high molecular weight polyethylene, available through Honeywell Incorporated. The cavities were filled with various flavor formulations such as PEG 3350 (68%), H&R spray dried flavor #813581 (28%) and sodium saccharin (4%). Approximately 0.030 grams of flavor were loaded into the cavities. The loading of 0.030 grams of flavor formulation is 40 times greater than what could be delivered from the 19.05 mm length of floss in the head using a conventional delivery system. The cavities were filled by hand, where a spatula was dipped into a melted formula and manually placed into the cavity. The cavities may also be filled by using a mechanized system where miniature pistons pump in the exact amount of flavor into the cavity via a heated nozzle system. The cavity's volume may be at least 0.1343279 cu. mm., more preferably the volume may be 0.026511 cu. mm.

An Arbor Press was used to create the flanges. The molded head was placed into a die to securely hold it. A 15.88 mm diameter rod was mounted to the ram of the press. Mechanical stops were used to stop the ram in varying positions, which in turn created different flange protrusions and lengths.

EXAMPLE 3

Dental Flossing Device

A dental flossing device was assembled by placing the cavity flavored-filled dental floss holder of Example 2 in the head portion of Example 1. The dental flossing device is shown in FIG. 1. The detents of the head portion receive the recesses of the dental floss holder. The recesses of the head portion receive the detents of the dental floss holder. The terminal snap fit recessions of the head portion receive the snap fit projections of the dental floss holder.

EXAMPLE 4

Flavored Dental Floss Device in Use

The dental floss device of Example 3 was assembled and placed in use. The dental floss holder was then given to individuals for an initial trial. The results showed a continuous flavor burst throughout the mouth during flossing of all the teeth. This result further shows that saliva does indeed activate the flavor system to deliver a strong flavor perception. It was found that blending the molecular weights of the polyethylene glycols used as the soluble substance could control the rate of flavor delivery into the oral cavity. Using 100% polyethylene glycol 1000 as the soluble substance provides rapid flavor delivery. The low melting point and high solubility of this substance make it desirable to use polyethylene glycol or polyethylene glycol blends at a higher molecular weight to achieve product survivability under either higher heat or higher humidity conditions, which are often seen in delivering products to the shelf. For this reason a mixture of polyethylene glycol 3350 with 5 to 50% polyethylene glycol 1000 is more desirable. The delivery of flavor into the mouth is longer lasting and the product shelf life significantly lengthened.

EXAMPLE 5

Flavored Dental Floss Device in Use

The dental floss holding device of Example 2 was attached to a handle. Despite being snap-fit into place on the handle, the dental floss holding device retained the flavor composition. In contrast, a prior art dental floss holding device having a similarly shaped cavity filled with a flavor composition, but not having flanges, expelled the flavor composition from the cavity when the device was attached to the handle.

What is claimed:

1. A dental floss holder comprising:
   a base portion;
   a pair of spaced-apart jaws extending from the base portion to accommodate a length of dental floss therebetween, at least one of the spaced-apart jaws comprising at least one cavity for containing a composition comprising a flavor and/or a chemotherapeutic agent, the cavity comprising at least one flange extending outward from and along a portion of a first side wall of the cavity for retaining said composition within the cavity.

2. A dental floss holder according to claim 1, wherein the base portion defines a tongue having lateral engaging surfaces, each engaging surface having at least one detent and at least one recess, the detent and recess being laterally spaced apart and aligned with a complementary detent and recess on opposite engaging surfaces of a head portion of a handle.

3. A dental floss holder according to claim 2, wherein said handle is integrally connected to the base of the dental floss holder and extends therefrom.

4. A dental floss holder according to claim 3, wherein said handle comprises a head portion and an elongated portion;
   the head portion having a releasable engagement means between the handle and the dental floss holder for retaining the dental floss holder securely in position on the head portion of the handle during movement of the dental floss device in use;
   the head portion further having a portion for receiving said dental floss holder, said head portion having a transversely extending groove defined by a floor, lateral receiving walls, and terminal snap fit recessions, each of said receiving walls having at least one detent and at least one recess, the detent and recess being laterally spaced apart and aligned with a complementary detent and recess on the other receiving wall;
   wherein, on assembly, the tongue of the dental floss holder engages the transversely extending groove and the lateral engaging surfaces contact the lateral receiving walls to define the releasable engagement means, and the snap fit projections of the spaced-apart jaws engage the terminal snap fit recessions of the head portion to constitute snap fitting means.

5. A dental floss holder according to claim 3, wherein said handle is made of polypropylene.

6. A dental floss holder according to claim 1, wherein said dental floss holder is made of a co-polyester.

7. A dental floss holder according to claim 1, wherein said cavity contains a flavored composition.

8. A dental floss holder according to claim 1, wherein said cavity contains a chemotherapeutic agent.

9. A dental floss holder according to claim 1, wherein each spaced-apart jaw contains at least one cavity.

10. A dental floss holder according to claim 9, wherein each cavity contains first and second flanges.

11. A dental floss holder according to claim 10, wherein each of the first and second flanges extends from about 0.05 mm to about 1.02 mm over the composition within the cavity and is from about 0.25 mm to about 1.02 mm in length along the top of the cavity.

12. A dental floss holder according to claim 9, wherein each cavity comprises a second side wall substantially parallel to the first side wall, and further comprises first and second flanges, the first flange extending along a portion of the first side wall and the second flange extending along a portion of the opposite second side wall.

13. A dental floss holder according to claim 1, wherein the cavity comprises a second side wall substantially parallel to and opposite the first side wall, and further comprises first and second flanges, the first flange extending along a portion of the first side wall and the second flange extending along a portion of the opposite second side wall.

14. A dental floss holder according to claim 1, wherein the cavity comprises a plurality of flanges, each flange extending only along a portion of the length of the cavity.

* * * * *